(12) United States Patent
Bickford et al.

(10) Patent No.: US 9,011,670 B2
(45) Date of Patent: Apr. 21, 2015

(54) THREE-DIMENSIONAL METAL ION SENSOR ARRAYS ON PRINTED CIRCUIT BOARDS

(75) Inventors: James A. Bickford, Winchester, MA (US); John R. Williams, Lexington, MA (US); Daniel I. Harjes, Allston, MA (US); Andrew Reiter, Boxborough, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 956 days.

(21) Appl. No.: 12/541,454

(22) Filed: Aug. 14, 2009

(65) Prior Publication Data

US 2010/0176006 A1 Jul. 15, 2010

Related U.S. Application Data

(60) Provisional application No. 61/088,770, filed on Aug. 14, 2008, provisional application No. 61/159,354, filed on Mar. 11, 2009.

(51) Int. Cl.
*G01F 1/64* (2006.01)
*G01N 27/333* (2006.01)

(52) U.S. Cl.
CPC .................................... *G01N 27/333* (2013.01)

(58) Field of Classification Search
USPC .......... 204/409–411, 416, 419, 422; 205/789, 205/789.5, 792.5, 790.5
See application file for complete search history.

(56) References Cited

U.S. PATENT DOCUMENTS

| | | | |
|---|---|---|---|
| 4,171,246 A | 10/1979 | Hamblen et al. |
| 4,530,029 A | 7/1985 | Beristain |
| 4,568,445 A | 2/1986 | Cates et al. |
| 4,592,824 A | 6/1986 | Smith et al. |
| 4,682,602 A | 7/1987 | Prohaska |
| 4,814,060 A | 3/1989 | Banks |
| 4,874,500 A | 10/1989 | Madou et al. |
| 4,946,562 A | 8/1990 | Guruswamy |
| 4,961,174 A | 10/1990 | Teel et al. |
| 5,050,035 A | 9/1991 | Hegner et al. |

(Continued)

FOREIGN PATENT DOCUMENTS

| | | |
|---|---|---|
| EP | 0990885 | 4/2000 |
| EP | 1306449 | 5/2003 |

(Continued)

OTHER PUBLICATIONS

Baselt, D.R. et al., "Design and Performance of a microcantilever-based hydrogen sensor," Sensors and Actuators B., Elsevior Sequoia S.A., Lausanne, CH., vol. 88, No. 2, pp. 120-131 (2003).

(Continued)

*Primary Examiner* — Luan Van
*Assistant Examiner* — Maris R Kessel
(74) *Attorney, Agent, or Firm* — Edward A. Gordon; Foley & Lardner LLP

(57) ABSTRACT

An electronic device includes a substrate and a plurality of sensors. Each sensor is disposed in a well over the substrate and includes a working electrode, an inner filling solution disposed thereover, and an ion-selective membrane. The working electrode is in contact with the substrate and the ion-selective membrane is disposed over the inner filling solution and substantially seals the well.

8 Claims, 16 Drawing Sheets

(56) References Cited

U.S. PATENT DOCUMENTS

| | | | |
|---|---|---|---|
| 5,063,081 A | 11/1991 | Cozzette et al. | |
| 5,156,810 A | 10/1992 | Ribi | |
| 5,183,549 A | 2/1993 | Joseph et al. | |
| 5,244,562 A | 9/1993 | Russell | |
| 5,259,247 A | 11/1993 | Bantien et al. | |
| 5,262,127 A | 11/1993 | Wise et al. | |
| 5,308,649 A | 5/1994 | Babacz | |
| 5,339,051 A | 8/1994 | Koehler et al. | |
| 5,348,649 A | 9/1994 | Mizuno et al. | |
| 5,417,115 A | 5/1995 | Burns | |
| 5,482,678 A | 1/1996 | Sittler | |
| 5,698,089 A | 12/1997 | Lewis et al. | |
| 5,741,409 A * | 4/1998 | Raguse et al. | 204/403.08 |
| 5,958,201 A | 9/1999 | Craig et al. | |
| 6,030,827 A | 2/2000 | Davis et al. | |
| 6,114,658 A | 9/2000 | Roth et al. | |
| 6,167,748 B1 | 1/2001 | Britton, Jr. et al. | |
| 6,447,449 B1 | 9/2002 | Fleischman et al. | |
| 6,457,750 B1 | 10/2002 | Sokurenko et al. | |
| 6,480,730 B2 | 11/2002 | Darrow et al. | |
| 6,534,316 B2 | 3/2003 | Strongin et al. | |
| 6,575,020 B1 | 6/2003 | de Charmoy Grey et al. | |
| 6,653,141 B2 | 11/2003 | Singaram et al. | |
| 6,664,407 B2 | 12/2003 | James et al. | |
| 6,673,533 B1 | 1/2004 | Wohlstadter et al. | |
| 6,730,201 B1 | 5/2004 | Kuhlman et al. | |
| 6,746,960 B2 | 6/2004 | Goodman | |
| 6,797,152 B2 | 9/2004 | Freund et al. | |
| 6,804,544 B2 | 10/2004 | Van Antwerp et al. | |
| 6,805,781 B2 | 10/2004 | Sørensen et al. | |
| 6,835,553 B2 | 12/2004 | Han et al. | |
| 6,872,297 B2 | 3/2005 | Mansouri et al. | |
| 6,896,778 B2 | 5/2005 | Lauks | |
| 6,916,660 B2 | 7/2005 | Wang et al. | |
| 6,927,246 B2 | 8/2005 | Noronha et al. | |
| 6,933,164 B2 | 8/2005 | Kubena | |
| 6,968,743 B2 | 11/2005 | Rich et al. | |
| 7,078,554 B2 | 7/2006 | Daniloff et al. | |
| 7,086,288 B2 | 8/2006 | Lee et al. | |
| 7,101,472 B2 | 9/2006 | Dineen et al. | |
| 7,105,352 B2 | 9/2006 | Asher et al. | |
| 7,186,566 B2 | 3/2007 | Qian | |
| 7,244,394 B2 | 7/2007 | Carney et al. | |
| 7,254,008 B2 | 8/2007 | Xie et al. | |
| 7,297,548 B2 | 11/2007 | Kawanishi et al. | |
| 7,305,883 B2 | 12/2007 | Khuri-Yakub et al. | |
| 7,306,672 B2 | 12/2007 | Hansen et al. | |
| 7,316,899 B2 | 1/2008 | McDevitt et al. | |
| 7,358,094 B2 | 4/2008 | Bell et al. | |
| 7,402,425 B2 | 7/2008 | Weinberg et al. | |
| 2003/0019299 A1 | 1/2003 | Horie et al. | |
| 2003/0027351 A1 | 2/2003 | Manalis et al. | |
| 2003/0186228 A1 | 10/2003 | McDevitt et al. | |
| 2003/0209451 A1 | 11/2003 | Dineen et al. | |
| 2003/0233882 A1 | 12/2003 | Mei | |
| 2004/0096357 A1 | 5/2004 | Majumdar et al. | |
| 2004/0180379 A1 | 9/2004 | Van Duyne et al. | |
| 2004/0231984 A1 | 11/2004 | Lauks et al. | |
| 2004/0256227 A1 * | 12/2004 | Shin et al. | 204/403.03 |
| 2005/0123442 A1 | 6/2005 | Gu et al. | |
| 2005/0158245 A1 | 7/2005 | Lakowicz et al. | |
| 2005/0196877 A1 | 9/2005 | Weinberg et al. | |
| 2005/0265914 A1 | 12/2005 | Gu et al. | |
| 2006/0116585 A1 | 6/2006 | Nguyen-Dinh et al. | |
| 2006/0148096 A1 | 7/2006 | Jina | |
| 2006/0155179 A1 | 7/2006 | Muller et al. | |
| 2006/0178572 A1 | 8/2006 | March | |
| 2007/0036682 A1 | 2/2007 | Gu et al. | |
| 2007/0105176 A1 | 5/2007 | Ibey et al. | |
| 2007/0110672 A1 | 5/2007 | Bellott et al. | |
| 2008/0020478 A1 | 1/2008 | Lowe et al. | |
| 2008/0039792 A1 | 2/2008 | Meng et al. | |
| 2008/0074661 A1 | 3/2008 | Zhang et al. | |
| 2008/0135409 A1 * | 6/2008 | Sakuraoka et al. | 204/403.01 |
| 2009/0014340 A1 | 1/2009 | Williams et al. | |
| 2009/0320606 A1 | 12/2009 | Carlen et al. | |

FOREIGN PATENT DOCUMENTS

| | | |
|---|---|---|
| JP | 01311240 | 12/1989 |
| WO | WO-9930144 | 6/1999 |
| WO | WO-00/10007 | 2/2000 |
| WO | WO-0171336 | 9/2001 |
| WO | WO-02/058551 | 8/2002 |

OTHER PUBLICATIONS

Chatzandroulis, S., "Fabrication of single crystal Si cantilevers using a dry release process and application in a capacitive-type humidity sensor", Microelectronic Engineering, Elsevier Publishers BV., Amsterdam NL, vol. 61-62, pp. 955-961 (2002).

Pepper, J. et al., "Detection of proteins and intact microorganisms using microfabricated flexural plate silicon resonator arrays", Sensors and Actuators B., Elsevior Sequoia A.S., Lausanne, CH., vol. 96, No. 3, pp. 565-575 (2003).

Baker et al. "Label-Free Sugar Detection Using Phenylboronic Acid-Functionalized Piezoresistive Microcantilevers," Anal Chem. 80 (13), Jul. 1, 2008, pp. 4860-4865.

Bakker et al. "Ion Sensors: Current Limits and New Trends," Analytica Chimica Acta, vol. 393, Issues 1-3, Jun. 30, 1999, pp. 11-18.

Buehler et al. "Designating a Water-Quality Monitor with Ion Selective Electrodes," Aerospace Conference, 2001, IEEE Proceedings, vol. 1, 2001, pp. 1/331-1/337.

Kanayama "Interfacial Recognition of Sugars by Boronic Acid-Carrying Self-Assembled Monolayer," Langmuir, 2000, 16, pp. 577-583.

Lei et al. "A Hydrogel-Based Implantable Micromachined Transponder for Wireless Glucose Measurement," Diabetes Technology & Therapeutics, vol. 8, No. 1, Feb. 2006, pp. 112-122.

Pribyl et al. "Quartz Crystal Biosensor for Detection of Sugars and Glycated Hemoglobin," Analytica Chemica Acta, vol. 530, No. 1, Feb. 7, 2005, pp. 75-84.

Takahashi et al. "Phenylboronic Acid Monolayer-Modified Electrodes Sensitive to Sugars," Langmuir, vol. 21, No. 11, May 24, 2005, pp. 5102-5107.

\* cited by examiner

THREE-DIMENSIONAL METAL ION SENSOR ARRAYS ON PRINTED CIRCUIT BOARDS

CROSS-REFERENCE TO RELATED APPLICATIONS

This application claims priority to and the benefit of U.S. Provisional Patent Application No. 61/088,770, filed on Aug. 14, 2008, and U.S. Provisional Patent Application No. 61/159,354, filed on Mar. 11, 2009, the disclosures of which are hereby incorporated herein by reference in their entirety.

FIELD OF THE INVENTION

The present invention relates, in various embodiments, to the fabrication of sensor arrays, and, in particular, to the fabrication of disposable sensor arrays capable of detecting a variety of analytes in solid, fluidic, and/or gaseous ambients.

BACKGROUND

Ion-selective electrodes ("ISEs") are sensors that measure the concentration of target ions (or "analytes") in a gas or solution. For example, the solution is exposed to an ion-selective membrane and a reference electrode. The ion-selective membrane produces an electromotive force ("EMF") (i.e., a voltage or electrical potential) proportional to the logarithm of the activity (which is approximately equal to the concentration) of the target ions. An ion-to-electron transducer layer may then convert the ion-based potential to an electron-based potential, which in combination with a reference electrode, may be detected by a typical voltage sensor. FIG. 1 illustrates a typical ISE 100 for measuring a concentration [I+]aq of ions in a solution 102. The ISE 100 includes a working electrode 104, a reference electrode 106, an ion-selective membrane 108, and an inner filling solution 110. The electrodes 104, 106 may include or consist essentially of a conductive material (such as platinum, copper, or silver). The working electrode 104 may be coated with an ion-to-electron transducing material, such as silver chloride. The inner filling solution 110 may include or consist essentially of conductive polymers, electrolytic solutions, and/or hydrogels, and may work with the ion-to-electron transducing material to convert ions, passed from the solution 102 through the membrane 108, to electrons. An insulator 112 prevents the solution 102 from coming into direct contact with, for example, the working electrode 104. Assuming that the ion-selective membrane 108 has a known, constant ion concentration [I+]org, the potential measured by the voltage meter 114 is proportional to log([I+]aq/[I+]org), and the unknown concentration [I+]aq may thus be derived from the potential.

One exemplary type of ISE is a single-ion ISE probe, available from a variety of manufacturers, such as Oakton Instruments of Vernon Hills, Ill., and Mettler-Toledo, Inc. of Columbus, Ohio. Single-ion ISE probes typically employ an inner filling solution 110 and a polyvinyl chloride ("PVC") membrane as the ion-selective membrane 108. These probes are generally cylindrical in shape and relatively large (e.g., approximately 3-4 inches in length and 0.5 inches in diameter) due to issues with manufacturing the inner filling solution.

Commercially available single-ion ISE probes typically have at least two different drawbacks that prevent their use in many applications. First, their relatively large size prohibits their use in size-constrained applications. Single-ion ISE probes are especially unsuitable for applications requiring the simultaneous measurement of multiple analytes in a constrained space because a large number of individual probes is typically required. Second, single-ion ISE probes may be prohibitively expensive, typically exceeding a cost of $400 per probe for a single analyte. In most applications, this high cost eliminates the possibility of a disposable device.

Another exemplary type of ISE, known as a solid-state ISE, features direct contact between the ion-selective membrane 108 and the working electrode 104 (i.e., there is no inner filling solution 110). Alternatively, the inner filling solution 110 may be replaced by some form of a solid material (e.g., a conductive polymer or lipophilic self-assembled monolayer). These all-solid formats allow arrays of solid-state ISEs to be screen-printed or electro-polymerized onto ceramic or plastic substrates.

Existing solid-state ISEs, however, are often unreliable and expensive. One problem occurs at a junction between the ion-selective membrane 108 and the insulating substrate 112. Over time, the aqueous sample solution 102 diffuses through the junction, causing a short circuit. This type of failure is especially common in plasticized PVC ISE membranes printed onto ceramic substrates. Poor material adhesion in such two-dimensional structures renders reliable sealing of the solution 102 difficult.

In addition, while recent research has produced a host of new, solid materials for use in place of the inner filling solution 110, they typically have not proven to be as electrically stable as traditional inner filling solutions described above. FIG. 2 illustrates the typical electrical instability of solid-state ISEs by depicting the response of a micro-electromechanical-system ("MEMS") based solid-state ISE over time. The initial response curve 202 drifts over time to curve 204 at day five, curve 206 at day fourteen, and curve 208 at day twenty-six. This changing of the response curve over time renders measurements of membrane potential irreproducible and inaccurate.

Thus, in order to service the demand for increasingly functional and accurate (yet disposable) sensor arrays, improved systems and methods for constructing high-density sensors are needed.

SUMMARY

Embodiments of the present invention include a miniature, disposable array of chemical-detection ISE sensors that may be deployed in a wide variety of environments. The ISE array may be fabricated on a standard printed-circuit board ("PCB") substrate or ground plane, which lowers both the cost and risk of manufacturing and development. In various embodiments, a robust, repeatable seal between the ion-selective membrane and a surrounding insulating structure improves the reliability of the sensor, as do tall, high-aspect-ratio ISE membranes over the working electrode.

Embodiments of the invention differ from prior art ISE-array devices in several aspects. For one, the embodiments described herein may include both inner filling solution-based ISEs and solid-state ISEs in a single miniature platform. In addition, prior-art ISE arrays are often screen printed or electro-polymerized onto a planar surface, thereby making it difficult to contain and control the shape of a multilayer ISE. Embodiments of the invention incorporate a user-defined three-dimensional well surrounding the working electrode, allowing the fabrication of accurately defined ISE layers over the electrode surface through, for example, a solution-casting technique (in which dissolved ISE material is injected into the well).

In general, in one aspect, embodiments of the invention feature an electronic device that includes a substrate and a plurality of sensors. Each sensor is disposed within a well over the substrate and includes a working electrode, an inner filling solution, and an ion-selective membrane. The working electrode contacts the substrate and the inner filling solution is disposed over the working electrode. The ion-selective membrane, disposed over the inner filling solution, substantially seals the well. A second plurality of sensors may also be disposed within wells under the substrate. Each of the second plurality of sensors may include a working electrode in contact with the substrate, an inner filling solution disposed over the working electrode, and an ion-selective membrane disposed over the inner filling solution. Again, the ion-selective membrane may substantially seal the well.

A cover may be disposed over a sub-array of the plurality of sensors. The cover may include or consist essentially of solder or a shape-memory alloy. An amplifier, conditioner, microprocessor, memory device, power source, and/or transmitter may be electrically connected to at least one sensor. In various embodiments, each well is disposed within a plate that is itself disposed over and in direct contact with the substrate. Each well may include a non-vertical sidewall, while the substrate may include a printed circuit board and/or a ground plane. A micro-fluidic front end may also be included to deliver a sample solution to the plurality of sensors. The micro-fluidic front end may include a micro-fluidic channel for temporally separating particles of different mass in the sample solution.

The plurality of sensors may be arranged in a two- or three-dimensional array, and the two-dimensional array may also temporally separate particles of different mass in the sample solution. Silver chloride may be disposed on the working electrode, the inner filling solution may include or consist essentially of a hydrogel and the ion-selective membrane may include or consist essentially of polyvinyl chloride.

In one embodiment, the inner filling solution includes a liquid that has a boiling point higher than 100° C. and that is capable of conducting ions. In various embodiments, an ion-conductive filter is disposed over the ion-selective membrane of a sensor.

In general, in another aspect, embodiments of the invention feature an ion-sensitive electrode that includes an ion-selective membrane for filtering an ion and a transducer for converting a potential of the ion into an electrical potential. A working electrode measures the electric potential. A solid-phase detection layer is disposed over the ion-selective membrane and dissolves a solid particle, thereby producing the ion. The solid-phase detection layer may include a hydrogel and/or methacrylamide or a similar chemical.

In general, in yet another aspect, embodiments of the invention feature a coated-wire ion-selective electrode that includes an inner filling solution and an electrically conductive wire disposed within the inner filling solution. An ion-selective membrane seals the inner filling solution. A transducer converts a potential of an ion filtered by the ion-selective membrane into an electrical potential for measurement by the wire. The inner filling solution may be a hydrated hydrogel, and the wire may include silver chloride. A plurality of coated-wire ion-selective electrodes may be arranged in a two- or three-dimensional array.

In general, in still another aspect, embodiments of the invention feature a method for fabricating an electronic device. The method includes forming a plurality of working electrodes and a plurality of wells, each substantially aligned with a working electrode, over a substrate. An inner filling solution is formed within at least one well and each well is then substantially sealed with an ion-selective membrane.

In one embodiment, the plurality of wells is disposed within a plate that is itself disposed over and in direct contact with the substrate. In this case, substantially sealing each well may include disposing the ion-selective membrane over the well and in contact with a portion of the plate and dissolving (e.g., by applying a solvent) at least a portion of the ion-selective membrane and the portion of the plate in contact with the ion-selective membrane. In addition, a solid-phase detection layer may be formed over at least one well, and a cover may be formed over a sub-array of the plurality of wells.

In general, in yet another aspect, embodiments of the invention feature a method of detection. The method includes disposing a plurality of sensors described above within an ambient comprising a first analyte and measuring an electromotive force resulting from passage of the first analyte into the ion-selective membrane of at least one sensor.

In some embodiments, the cover disposed over a sub-array of a plurality of sensors is removed before measuring the electromotive force. A signal, corresponding to the electromotive force, may be transmitted to a remote location. In various embodiments, an electromotive force, resulting from contact between a second analyte in the ambient and the ion-selective membrane of at least one sensor, is also measured.

Each of the plurality of sensors may be disposed within a well over a substrate. The working electrode may be an electrically conductive wire. The first analyte may include a solid particle and the solid particle may be dissolved by a solid-phase detection layer disposed in contact with the ion-selective membrane. The inner filling solution may include a high-boiling point fluid. The first analyte may be separated from the ambient, prior to measuring the electromotive force, based on a mass of the first analyte.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

Figure 1:
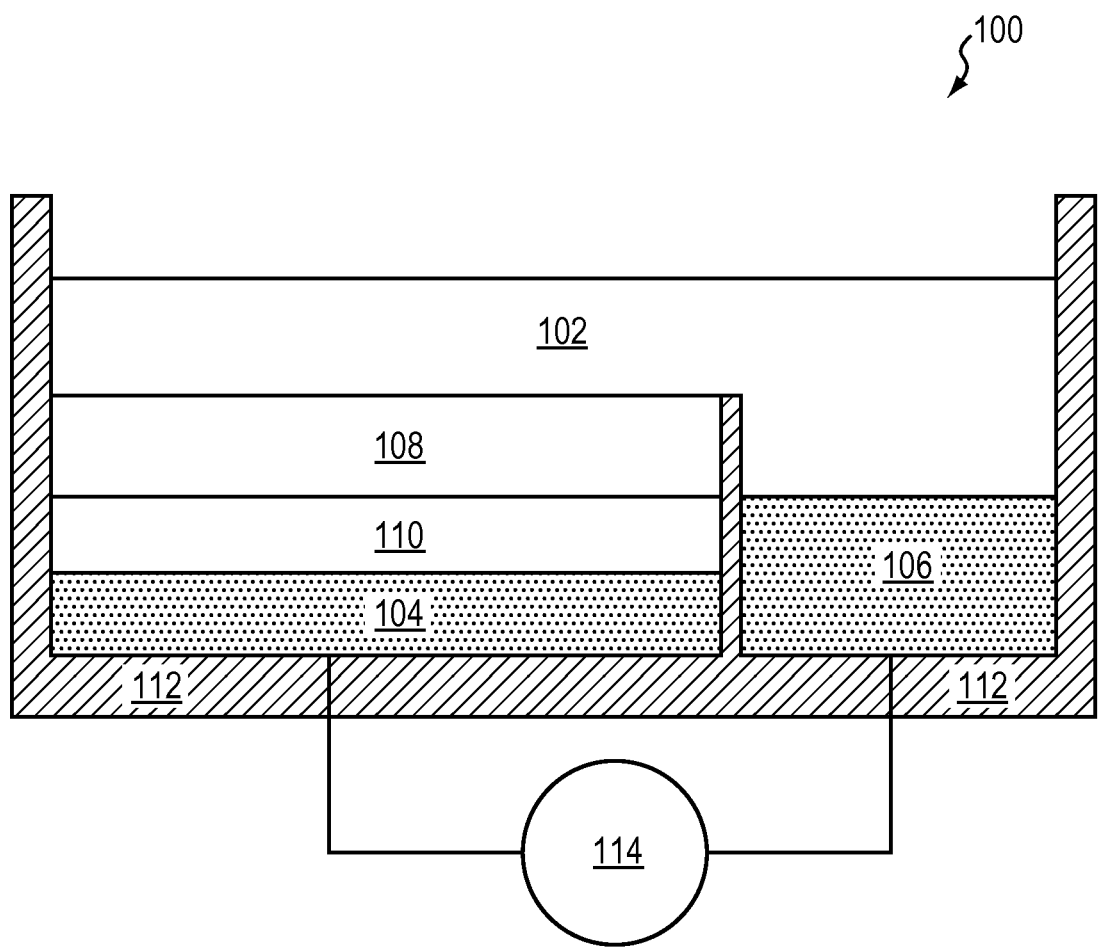
FIG. 1 illustrates an exemplary prior-art ISE.
Figure 2:
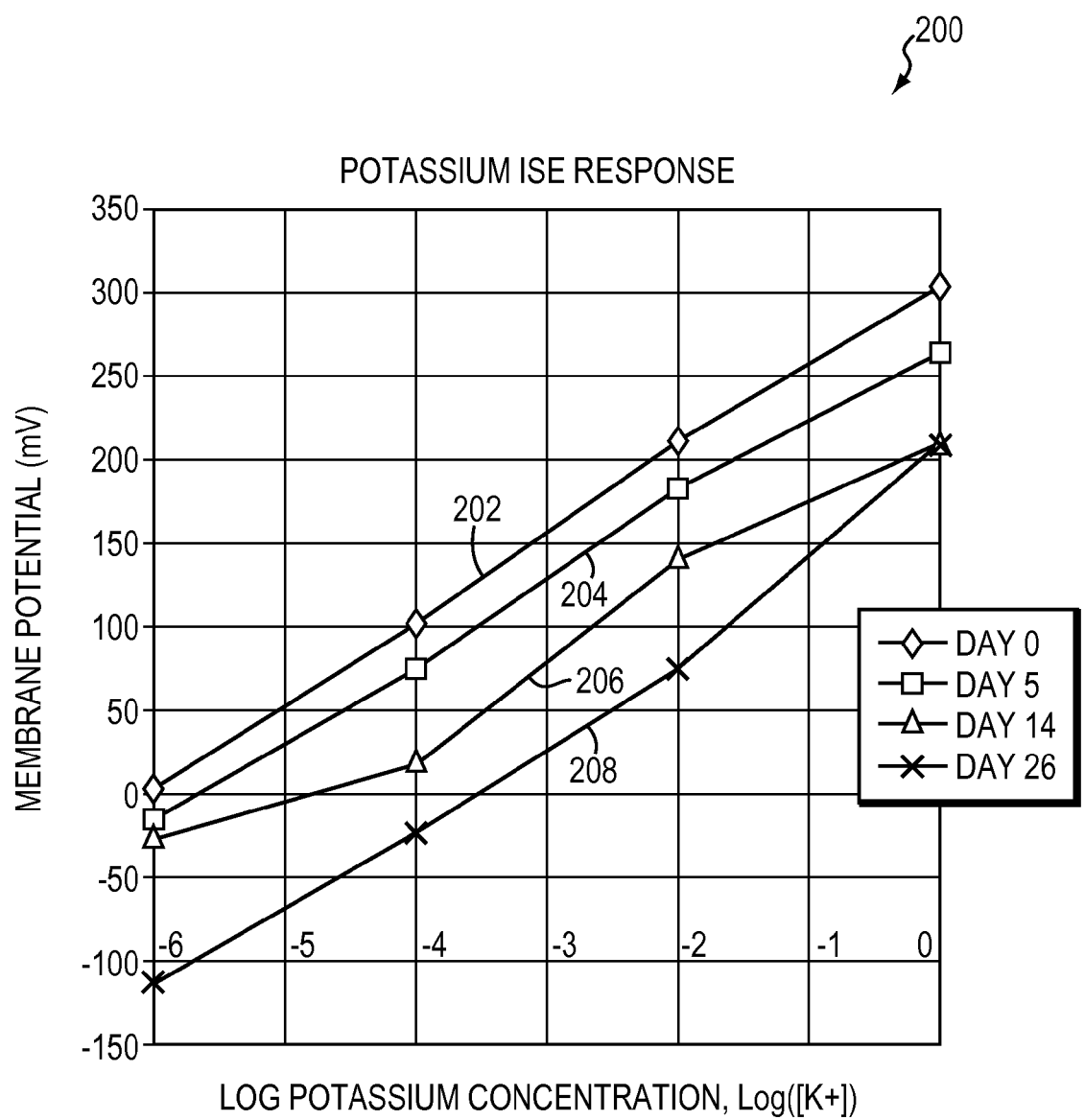
FIG. 2 is a graph illustrating how the response of an exemplary prior-art solid-state ISE changes over time.
Figure 3A:
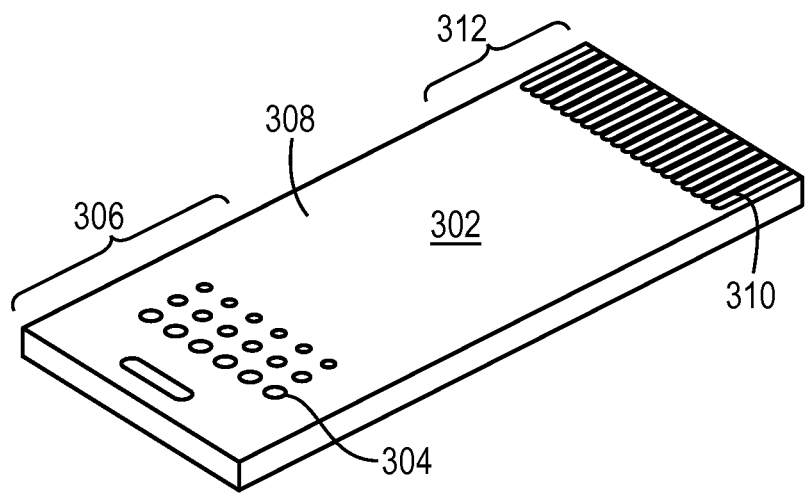
FIGS. 3A, 3B, 4A, and 4B illustrate printed-circuit boards in accordance with embodiments of the invention.

FIG. 3A illustrates an embodiment of the invention featuring a PCB 302 with small (approximately 0.100 inch or smaller diameter) pads 304 patterned in a first region 306 of a first surface 308 of the PCB 302. As described further below, an ISE may be formed on each pad 304. The pads 304 may be spaced by an approximately 0.050 inch pitch, resulting in a sensor density of approximately 400 sensors per square inch. Additional pads 304 for additional ISEs may be patterned on a second surface of the PCB 302 (e.g., the face-down surface of the PCB 302, which is not shown). The pads 304 are electrically connected through the interior of the PCB 302 to output leads 310 formed on another part 312 of the PCB 302. The output leads 310 allow the measurement of the EMF generated by the ISEs formed on each pad 304 of the PCB 302 during ISE operation. Depending on the ISE requirements, the pads 304 may be plated with a thin layer of gold, silver, solder, or other appropriate working-electrode material. The PCB 302 may include embedded shielding layers to reduce noise and drift error terms generated by, for example, electrostatic charge build-up.

Figure 3B:
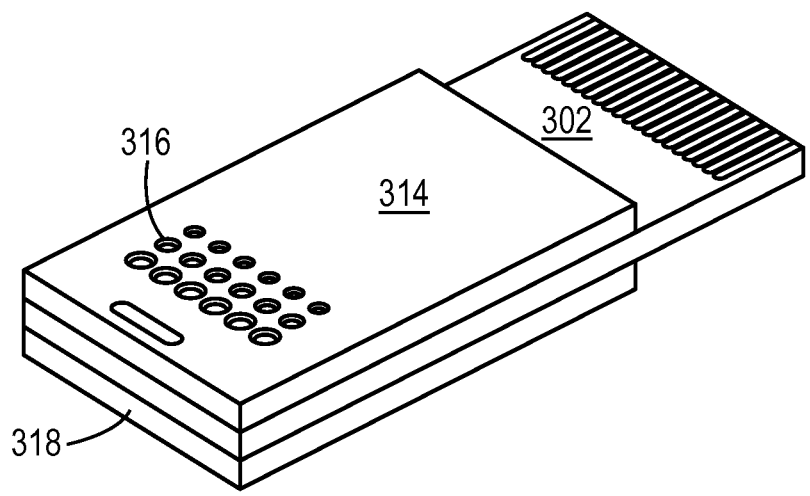

FIG. 3B illustrates a stiffening layer 314 (e.g., a pre-drilled polymer plate) that may be attached to the surface 308 of the PCB 302 with, for example, a lamination process. Wells 316 may be drilled into the stiffening layer 314 prior to or subsequent to lamination to allow access to the pads 304, thereby creating cavities surrounding each pad 304. Each well 316 may be substantially aligned with a pad 304 such that all or most of the pad 304 is exposed by the corresponding well 316. In one embodiment, the exposed portion of the pad 304 is sufficient to provide an electrical connection to an ISE formed in the corresponding well 316 without adding an appreciable amount of electrical resistance to the connection. A second stiffening layer 318 may be attached to the second, face-down, surface of the PCB 302, thereby creating similar cavities surrounding the pads on the second surface of the PCB 302.

Figure 4A:
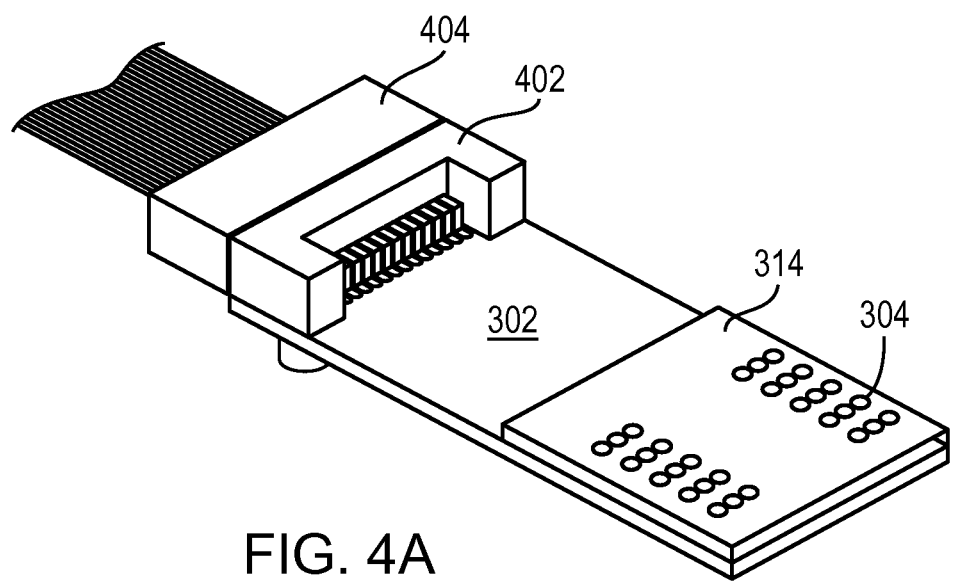
Figure 4B:
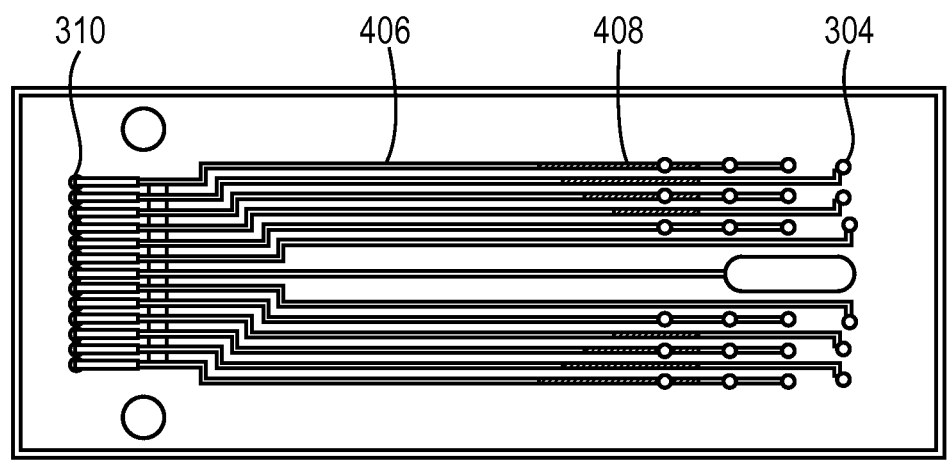

FIG. 4A illustrates another embodiment of the PCB 302 and stiffening layer 314 in which the output leads 310 are connected to a PCB connector interface 402, which in turn is connected to a cable 404. The interface 402 and cable 404 may be standard, off-the-shelf components. FIG. 4B illustrates an exemplary wiring diagram for the internal routing of the PCB 302. The PCB 302 may feature one or more internal metal layers 406, 408 that connect the pads 304 with the output leads 310.

In an alternative embodiment, layers similar to the stiffening layers 314, 318 are added to the PCB 302 to form wells 316 around the pads 304 using a two-part liquid urethane cast. In such a casting process, a two-piece negative mold, with posts covering the electrode pads 304, is clamped around the PCB 302. An encapsulant, such as a liquid urethane or silicone, is then injected between the PCB 302 and the mold. After the encapsulant is cured, the mold is removed. Other than holes (corresponding to the location of the mold posts) exposing the electrode pads 304, the PCB 302 may be completely encapsulated by the encapsulant.

Figure 5:
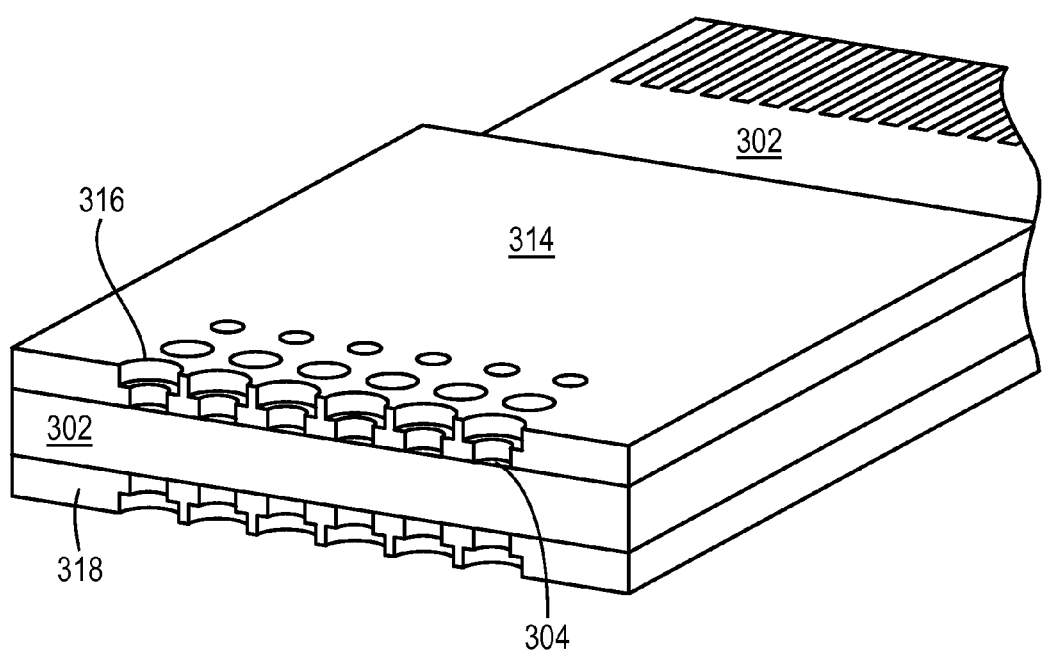
FIG. 5 illustrates a cross-section of a printed-circuit board in accordance with one embodiment of the invention.
Figure 6:
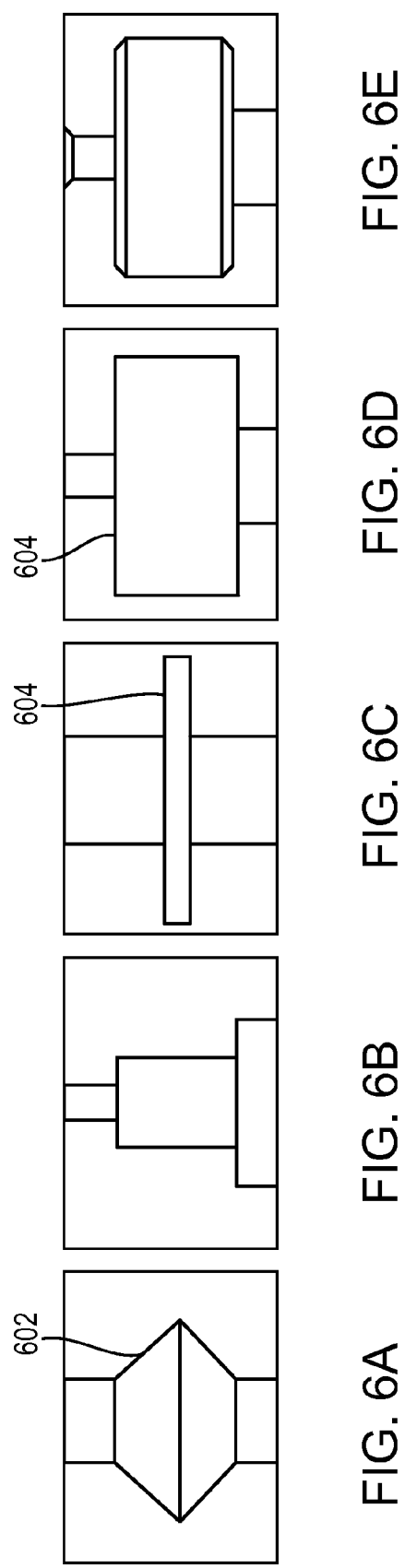
FIGS. 6A-6E illustrate sample wells in accordance with embodiments of the invention.

FIG. 5 illustrates a cross-sectional view of the PCB 302, wells 316, pads 304, and stiffening layers 314, 318. As further illustrated in FIGS. 6A-6E, the wells 316 may have a variety of different cross-sectional shapes. For example, the wells 316 may have a tall aspect ratio (i.e., be taller than they are wide) to increase electrical stability over time. More specifically, a tall aspect ratio provides an ISE with a greater ratio of volume to surface area, reducing component diffusion out of the well 316 and increasing electro-chemical stability. In addition, the wells 316 may incorporate overhangs and/or chamfers to increase membrane adhesion and facilitate formation of a labyrinth seal therein. In particular, the wells 316 may include non-vertical sidewalls, such as diagonal sidewalls 602 or horizontal or substantially horizontal sidewalls 604.

Moreover, with wells 316 having a tall aspect ratio, thicker ion-selective membranes may be formed inside the wells 316, thereby increasing the surface area of contact between the ion-selective membranes and the sidewalls of the wells 316. This increases the bonding area between the two materials, which, in turn, may increase the strength of the bond between each ion-selective membrane and its well's sidewalls. In general, a stronger bond decreases the likelihood of a bond failure, thereby decreasing the chance that an ambient solution or gas will circumvent the ion-selective membrane and make direct contact with the working electrode. As such, sensor reliability is improved.

Because embodiments of the invention may employ standard PCB technology, a myriad of available off-the-shelf components may be added to the PCB without modification. For example, local signal amplifiers and conditioners may be employed to reduce sensor noise, especially if a sensor signal needs to be routed over long distances (i.e., has a long track length). Digital circuitry, such as microprocessors, flash memory, and power sources, may also be added to create a self-contained data logging device. The additional incorporation of a radio-frequency, ultrasonic, or optical (e.g., infrared) transmitter may permit wireless transmission of the sensor data, which may be beneficial when assessing analyte levels in environments where retrieval of the device is difficult, such as in hazardous environments (e.g., radioactive sites), lunar/planetary missions, and/or covert applications.

Figure 7:
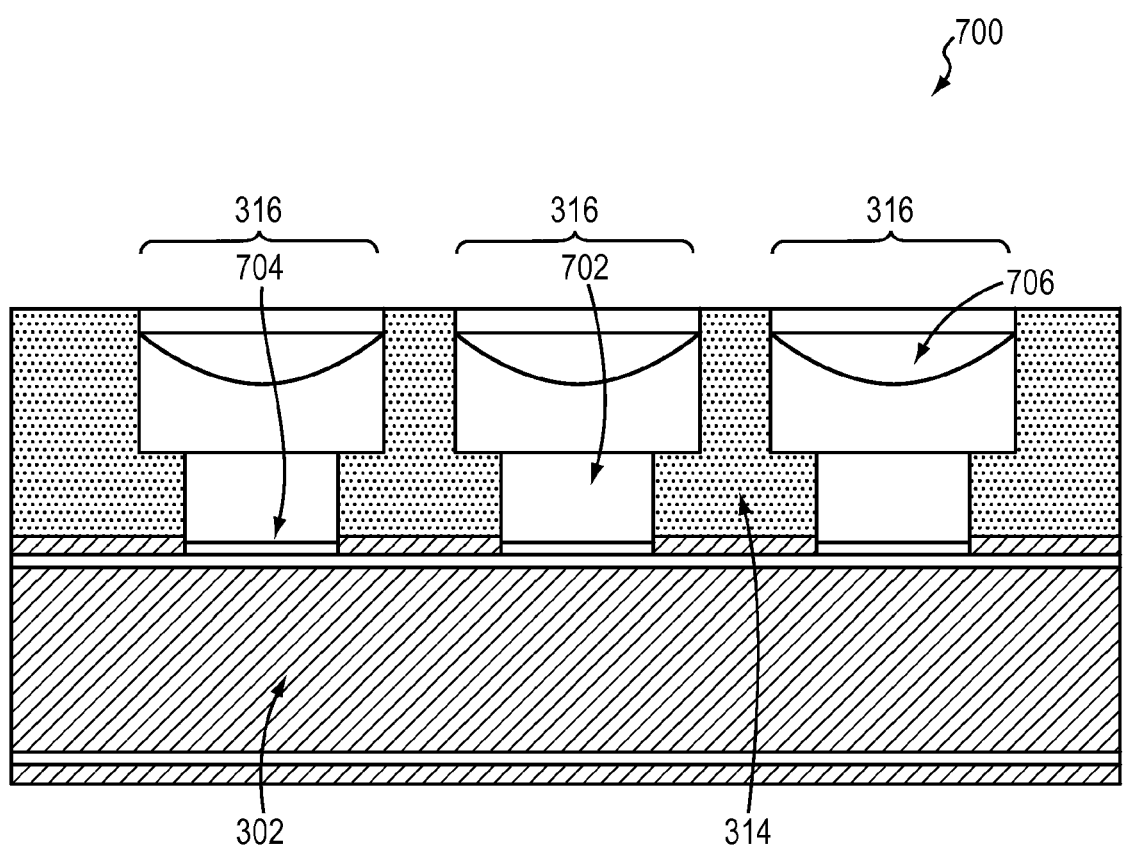
FIG. 7 illustrates a layered ISE structure in accordance with one embodiment of the invention.

FIG. 7 illustrates a layered ISE structure 700 in accordance with one embodiment of the invention. Once the wells 316 are fabricated in the stiffener/polymer layer 314, as described above, each well 316 is filled with various layers, such as membranes and transducers, to form an ISE. In one embodiment, the ISE includes an inner filling solution 702, which may include or consist essentially of an electrolytic solution and/or a hydrogel. The ISE may also include a working electrode 704 in contact with the PCB substrate 302. The working electrode 704 may include a copper or platinum surface-mount technology pad, and, in one embodiment, is coated with silver or silver chloride, which may function as an ion-to-electron transducer. The hydrogel of the inner filing solution 702 may be hydrated or saturated with a salt solution depending on the type of coating on the working electrode 704, for example a 1.0 molar potassium chloride ("KCl") in water in the case of a silver chloride coating. One of skill in the art will realize that other types of working electrodes 704 and inner filling solutions 708 are within the scope of the invention. An ion-selective membrane 706 covers the inner filling solution 702 and filters an analyte or analytes of interest. Examples of target analytes include sodium, potassium, calcium, chloride, nitrate, sulfate, and even heavy-metal ions such as mercury, lead, and uranyl (i.e., aqueous uranium oxide). In one embodiment, a silver chloride ion-to-electron transducer accepts electrons from the working electrode 704 (provided by an electrical circuit connected to the working electrode 704) and combines them with chloride, which, together with the inner filling solution 702, causes a release of Cl⁻ ions into the adjacent ion-selective membrane 706. Thus, the silver chloride ion-to-electron transducer layer and the inner filling solution 702 work in conjunction with the ion-selective membrane 706 to transform electron flow into ion flow.

Alternatively, the inner filling solution 702 may be replaced by a conductive polymer, such as Poly(3,4-ethylenedioxythiophene) poly(styrenesulfonate) ("PEDOT:PSS"). A solution-cast PVC layer, containing a specific ionophore (and optional additives), may then cover the conductive polymer layer to form an ion-selective membrane. The conductive polymer layer exchanges ions directly with the PVC ion-selective membrane. Each well 316 may be an independent sensor, capable of detecting a particular target (e.g., $K^+$, $Na^+$, $Pb^{2+}$, $[UO_2]^{2+}$, etc.).

In one embodiment, the inner filling solution 702 includes or consist essentially of a water-based solution. In an alternative embodiment, the inner filling solution 702 includes or consists essentially of a non-water-based solution having low volatility. As further described below, the reduction or elimination of water-based solutions in the inner filling solution 702 may extend sensor lifetime by minimizing the evaporation rate and loss through the membrane 706.

The ISE may operate in conjunction with a reference electrode or reference cell. The reference electrode may be fabricated in a manner similar to the ISE, but with the ion-selective membrane 706 replaced by, for example, a porous ceramic or a non-selective ionically conductive polymer layer. Alternatively, another ISE may be utilized as the reference electrode. For example, a potassium ISE with a hydrogen ISE reference enables the measurement of the ratio of potassium concentration to pH.

Embodiments of the invention feature the chemical "welding" of an ion-selective plasticized PVC membrane 706 to the well structure (i.e., a technique distantly analogous to a solder re-flow technique), thus forming a highly robust seal and diminishing the chances of a short circuit. This chemical welding may be accomplished by exposing the device to a first vaporized solvent that dissolves at least a portion of the ion-selective membrane 706, for example an organic solvent such as acetone, cyclohexanone, toluene, or tetrahydrofuran ("THF"). The first solvent preferably does not dissolve or minimally dissolves the surrounding well structure. The dissolving of the ion-selective membrane 706 protects the underlying well structure through the rest of the process. A second vaporized solvent that dissolves at least a portion of one or both of the ion-selective membrane 706 and the surrounding insulating well structure (e.g., methyl ethyl ketone) is then applied to the device, "chemically welding" the two together at the points where the dissolved portions of the layers meet. The bond that forms between the ion-selective membrane 706 and the well structure substantially seals the well (i.e., hermetically seals the interface between the ion-selective membrane 706 and the well from an ambient solution or gas, while still allowing ions to pass through the ion-selective membrane 706).

Figure 8:
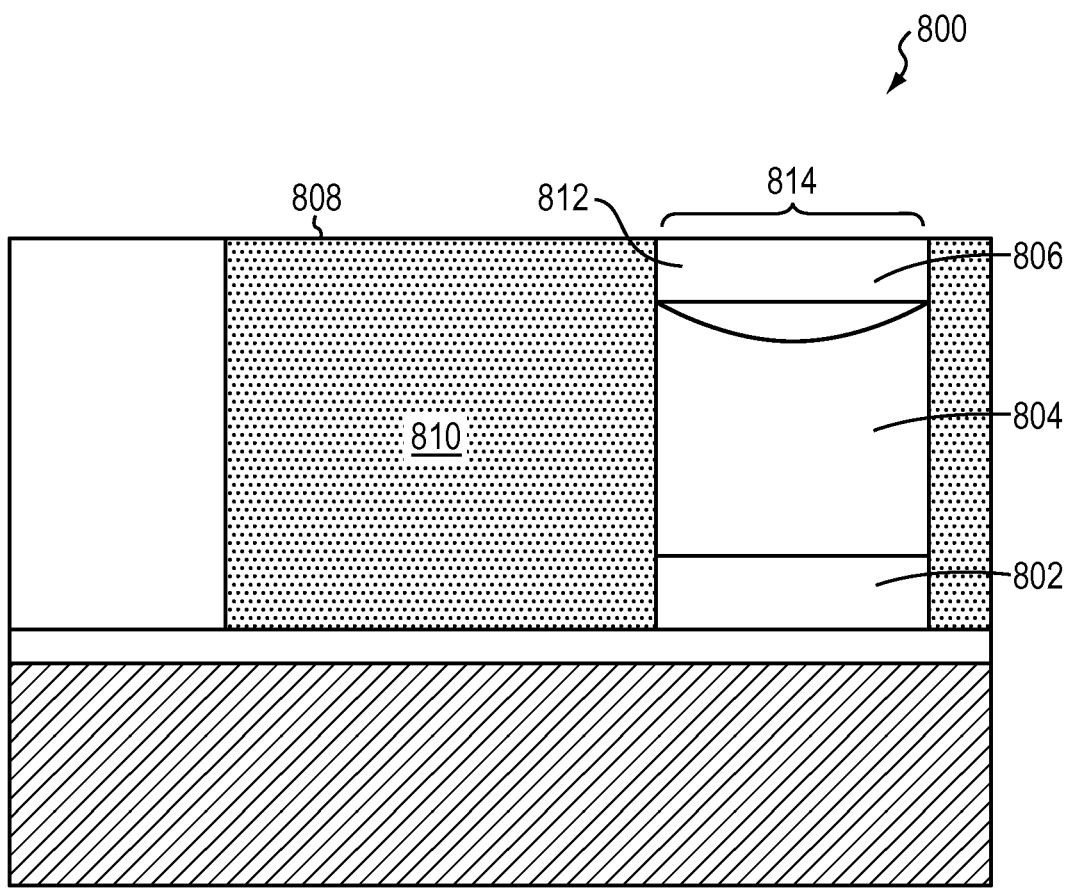
FIG. 8 illustrates a solid-state ISE in accordance with one embodiment of the invention.

FIG. 8 illustrates one embodiment of a solid-state ISE that functions without an inner filling solution. The solid-state ISE layer structure 800 includes copper PCB pads 802 coated with silver and/or silver chloride and an ion-selective membrane 804 (e.g., polyvinyl chloride) in direct contact therewith. A top surface 806 of the ion-selective membrane 804 may be below a top surface 808 of a surrounding support structure 810, thereby exposing an interior sidewall 812 of the well 814. In another embodiment, the top surfaces 806, 808 are substantially coplanar.

Embodiments of the invention may be utilized in a variety of applications, including, for example, water quality monitoring systems, sensors for remotely operated vehicles, analysis of clinical blood sera (e.g., of blood electrolyte levels), clinical urine analysis, drug discovery (e.g., extracellular ion signaling), terrestrial and extraterrestrial soil analysis, explosive residue detection (e.g., nitrates, F, and/or Cl), and/or agriculture and food monitoring. In some embodiments, an application requires the detection of multiple analytes present in a single solution. In these embodiments, different types of ion-selective membranes may be used, wherein each type selects a different analyte. For example, a first ion-selective membrane may select a first analyte and a second ion-selective membrane may select a second analyte. Thus, the presence and/or concentration of the first and second analytes may be determined by different ISEs formed on the same PCB. As described above, the presence and/or concentration of each analyte may be determined by measuring the electromotive force resulting from the contact between that analyte and the ion-selective membrane of the ISE in question.

Further features that may be employed in accordance with various embodiments of the invention are described below.

A. Diffusion Channels

ISE sensors fabricated in accordance with various embodiments of the invention may be coupled to diffusion channels in order to provide feedback as a function of time (thus aiding chemical differentiation and accuracy) and to minimize potential fouling of the ISE by other materials in the sampled solution. Each diffusion channel may include or consist essentially of a long narrow channel between the ISE sensor and the sample solution. The diffusion of ions through the channel is substantially proportional to their size; thus, smaller ions are detected by the ISE sensors before larger ones. The diffusion channels may operate in a fashion similar to gas chromatography columns in gas chromatography-mass spectrometry techniques.

B. Electrically Activated Array Covers

Figure 9:
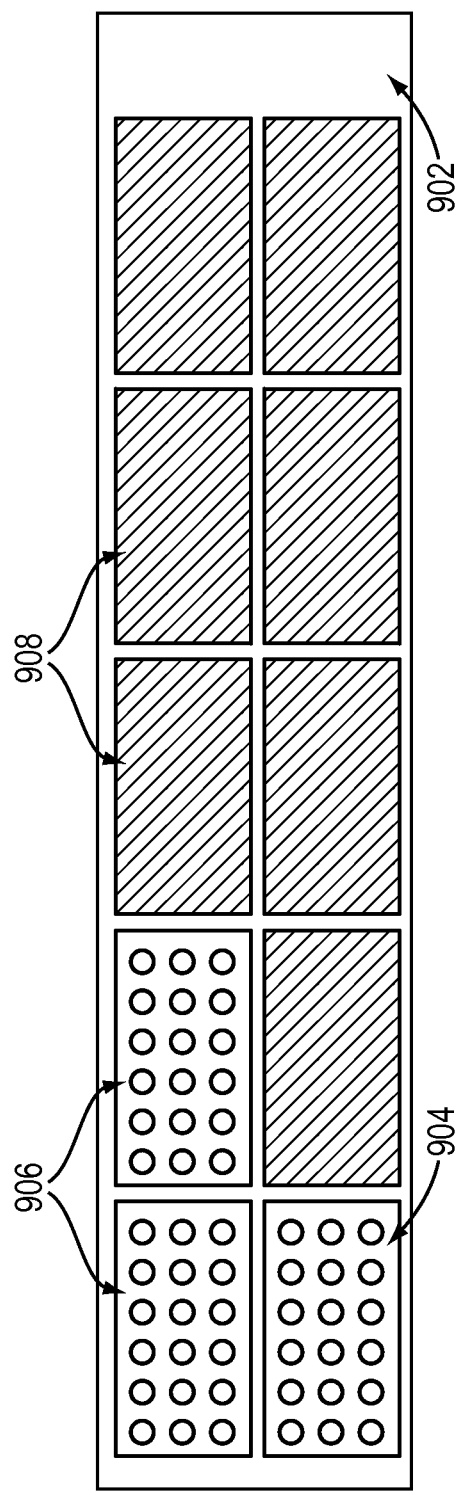
FIG. 9 illustrates electrically activated array covers in accordance with embodiments of the invention.

For many applications, it is desirable to have only approximately 30 individual ISE sensors (e.g., three sensors for each of ten analytes). Embodiments of the invention, however, are capable of populating a square inch of a PCB with approximately 400 ISE wells, far exceeding many application requirements. To leverage this sensor density, and with reference to FIG. 9, arrays of ISE sensors 904 may be sectioned off into separate sub-arrays 906. Each sub-array 906 may be independently capable of performing individual system requirements, and may be hermetically sealed using a thin solder cover 908 or shape-memory alloy. For clarity, FIG. 9 illustrates a PCB 902 having seven sub-arrays 906 that are covered with a thin solder 908, and three uncovered sub-arrays 906. When a current is passed through an electrically-activated cover 908, the internal resistance of the solder causes it to heat and melt. The respective sub-array 906 of ISEs 904 below the cover 908 are thereby exposed to the surrounding sample solution.

This technique may allow a single device to be used on numerous occasions. ISEs are generally reversible sensors, but certain compounds (e.g., strong acids, bases, or charged lipophilic compounds) may permanently damage the sensors. Using sub-arrays, the entire device is not ruined if an unknown sample proves harmful to an exposed sub-array 906 of ISEs; instead, a new sub-array 906 may be exposed. In addition, the output signal of the sensor array may be refined by the utilization of inputs from multiple sensors, allowing the estimation of cross-selectivity and other error terms.

C. Extended-Lifetime ISE Devices

Figure 10:
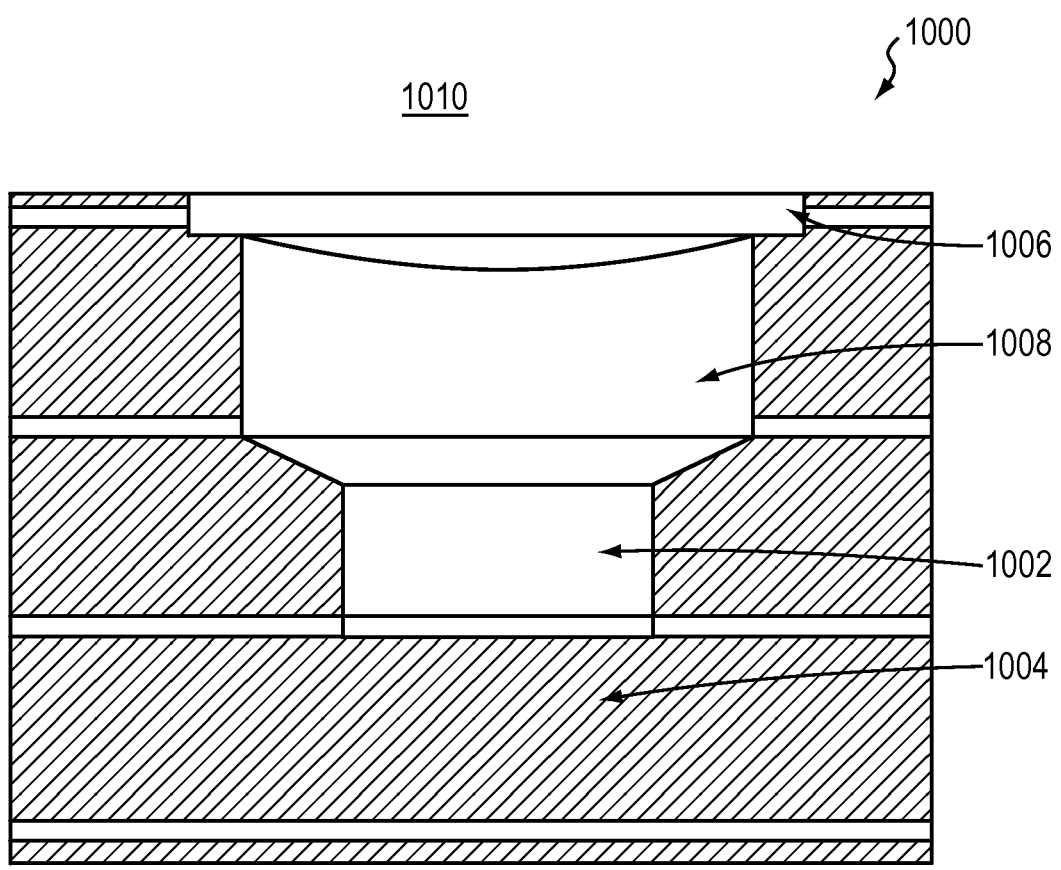
FIG. 10 illustrates an extended-lifetime ISE device in accordance with one embodiment of the invention.

ISEs typically require a water-based inner filling solution to dissolve and conduct ions. In low-pressure, high-temperature environments, or over extended periods of time in a dry environment, however, the water-based solution may evaporate through the ion-selective membrane and the sensor may cease to conduct ions (i.e., stop working). Accordingly, in one embodiment of the present invention, the water is replaced with a high-boiling-point liquid that dissolves and conducts the ionic species of interest. FIG. 10 illustrates one embodiment of a sensor 1000 in which the typical bulk inner filling solution or liquid in the saturated hydrogel layer 1002 is replaced with, for example, dimethyl sulfoxide, dimethyl formamide, ethylene glycol, and/or other ion-conducting liquids having a boiling point higher than that of water (i.e., higher than 100° C.). Use of the alternative liquid to conduct ionic species to an electrode 1004 may increase the lifetime of the sensor 1000 in harsh environments. In addition, an optional filter membrane 1006 may be added over the ion-selective membrane 1008 (which may be made of PVC) to prevent diffusion of components in and out of the ambient environment 1010, thereby further extending the operational lifetime of the sensor 1000.

D. Solid Phase Detection

Figure 11:
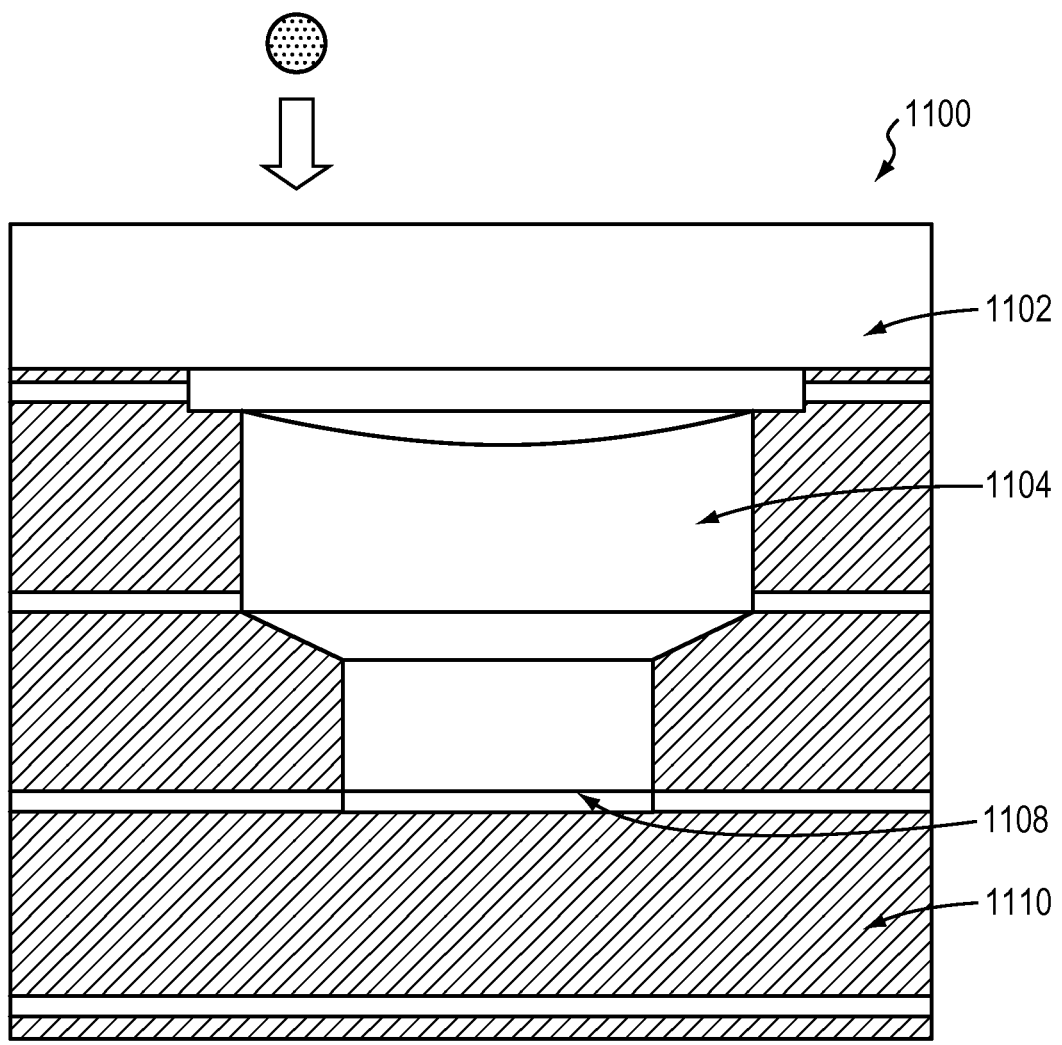
FIG. 11 illustrates a solid-phase detection ISE device in accordance with one embodiment of the invention.

ISEs are typically aqueous sensors that measure ion concentration in water solutions. However, certain applications require the direct analysis of solid particles. FIG. 11 illustrates, in one embodiment, a solid-phase detection layer 1102 placed over and in contact with an ion-selective membrane 1104 to dissolve a target solid particle 1106 directly into the device 1100. In a manner similar to electrophoresis, solid analytes may dissolve at the surface of the solid-phase detection layer 1102, and resulting ions may diffuse therein. The layer 1102 may be a hydrogel, and may include or consist essentially of methacrylamide or a chemical having similar characteristics. The dissolved species diffuse into the solid-phase detection layer 1102 and may be measured by the ISE 1100 via an electrode 1108. Electrostatic shielding in the form of a ground plane (e.g., in the PCB substrate 1110) may also be incorporated into the device design to reduce drift and noise effects caused by electrostatic build-up and external coupling.

E. Enhanced Coated Wire Electrode

Figure 12:
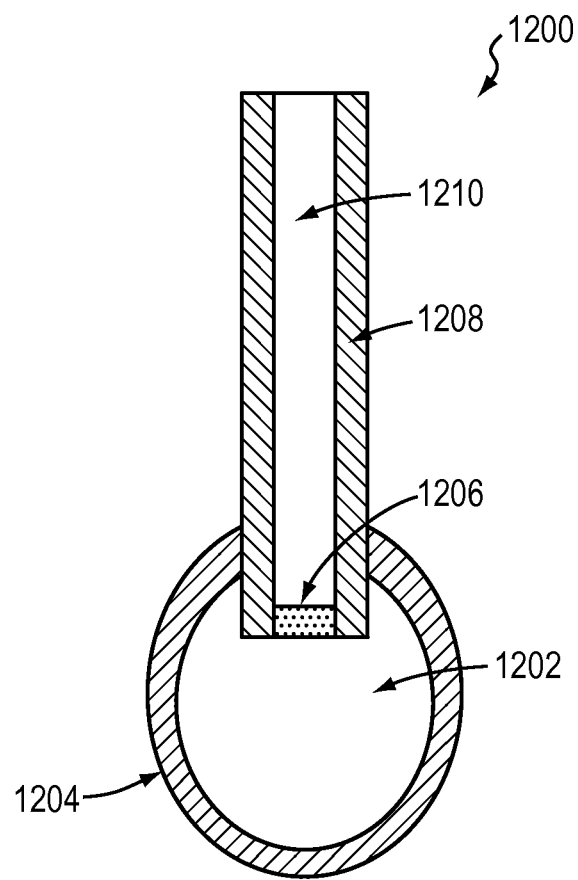
FIG. 12 illustrates an enhanced coated-wire electrode in accordance with one embodiment of the invention.

FIG. 12 illustrates a coated-wire ISE 1200 in accordance with one embodiment of the invention. Typically, coated-wire ISEs are fabricated by coating a bare silver chloride wire with an ion-selective membrane. While these devices are functional, they are highly unstable due to the lack of an inner filling solution. The coated-wire ISE 1200, however, features a hydrated hydrogel phase 1202 used to form an inner filling solution between the ion-selective membrane 1204 and the silver chloride working electrode 1206. The ion-selective membrane 1204 may be formed by dip-coating the coated-wire ISE 1200. An insulating layer 1208 electrically isolates a conductor core 1210 (which may include silver). The resulting ISE 1200 is small, easy to fabricate, and electrically stable. A plurality of such devices may be integrated together to form a fully packaged ISE array.

In various embodiments, a plurality of coated-wire ISEs 1200 may be arranged in a two- or three-dimensional array or other similar grouping. The two-dimensional array may be disposed on a surface of a substrate or PCB, and the three-dimensional array may be formed by disposing a plurality of substrates or PCBs in layers. In other embodiments, a three-dimensional array of coated-wire ISEs 1200 may be supported by a three-dimensional mesh or screen or by vertical structures extending from a flat surface. Two- and three-dimensional arrays of coated-wire ISEs 1200 may be area-efficient, thereby producing a high density of ISEs 1200 in a small area, which may be beneficial for area-constrained applications. The relative closeness of the ISEs 1200 may additionally ease the design and implementation of the electrical circuits required to read the sensor data. In addition, the two- or three-dimensional configuration of the ISEs 1200 may allow the sensors to track the diffusion and/or presence of analytes across two or three dimensions, which may be useful in some applications.

F. Integrated Front End

Figure 13:
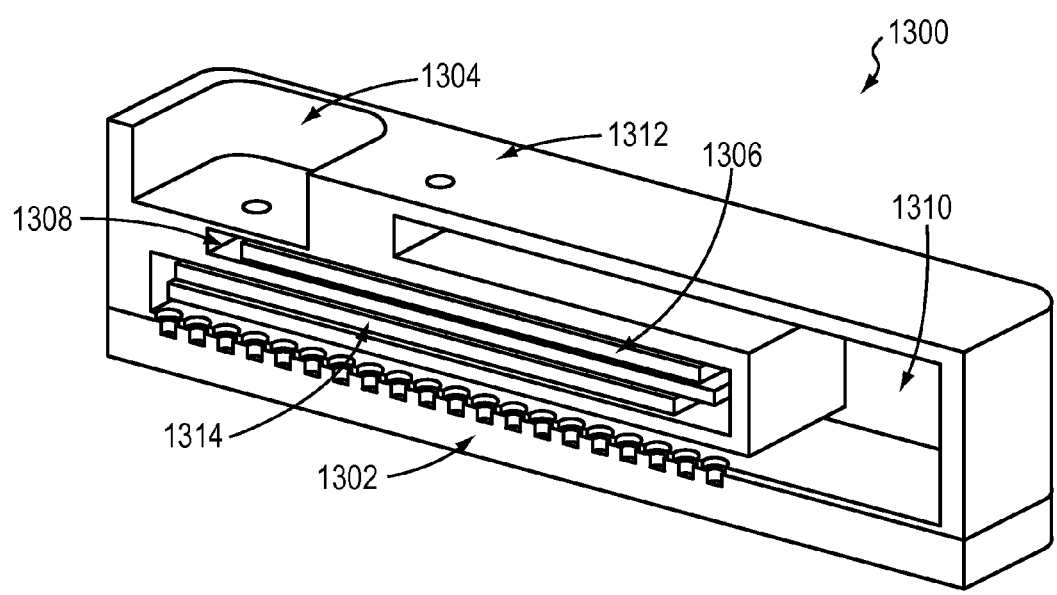
FIG. 13 illustrates an integrated front end in accordance with one embodiment of the invention.

FIG. 13 illustrates one embodiment of a micro-fluidic front end 1300 that improves the ability to deliver a sample to an ISE sensor or sensors 1302 while providing multiple calibration points. A fluidic sample 1306 is placed in a sample port 1304 and is drawn through a fluidic channel 1308 by, for example, a suction force from a vacuum chamber 1310. The vacuum force may be provided through a vacuum port 1312, which may be active (as shown) or sealed during manufacture if a vacuum is not required in a given application. Optionally, one or more calibration solutions 1314 may be drawn across the sensor array 1302 just prior to the sample solution 1306 being drawn across. The calibration solutions 1314 may be used in measuring a baseline EMF potential, thereby improving the quality of the measurement of the sample 1306.

The enclosed fluidic channel 1308 may also preserve the sample 1306 and/or the calibration fluid 1314 in a controlled, humid environment during non-operational periods, thereby preventing or delaying the evaporation of the samples 1306, 1314 and extending the time window in which an accurate measurement may be made. Furthermore, the channel 1308 may act as a diffusion channel and add a temporal variable to the data to reduce cross sensitivity from interferents and differentiated analytes. For example, if the analyte of interest is a small, light particle, it may reach the sensor array 1302 at an earlier time than a large, heavy particle that is not of interest. Blood samples, in particular, typically contain large particles (such as proteins) that may not be relevant to an analysis of the sample and may be temporally filtered using this method.

In one embodiment, a two-dimensional array of ISEs may be used to differentiate analytes by diffusion. In this embodiment, a solution containing differentiated analytes may be placed at a first position on or near the array. As the solution diffuses to other positions on the array, the different analytes may diffuse at different rates, which the ISEs may record across the two dimensions of the array.

G. Example

Figure 14A:
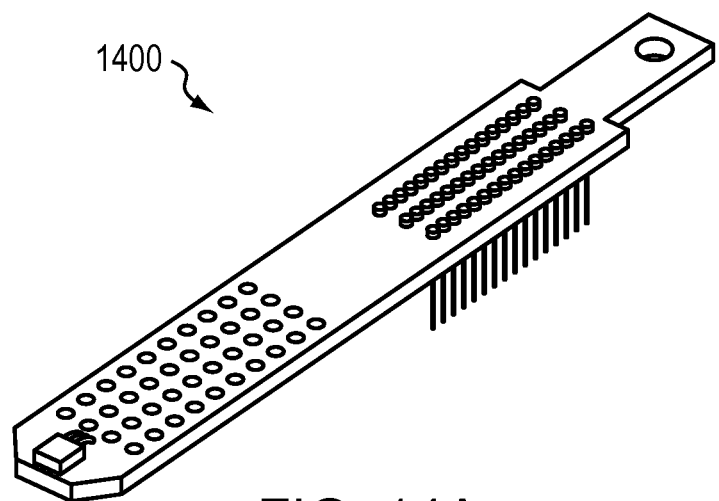
FIGS. 14A-14B illustrate an exemplary printed-circuit board in accordance with one embodiment of the invention.
Figure 14B:
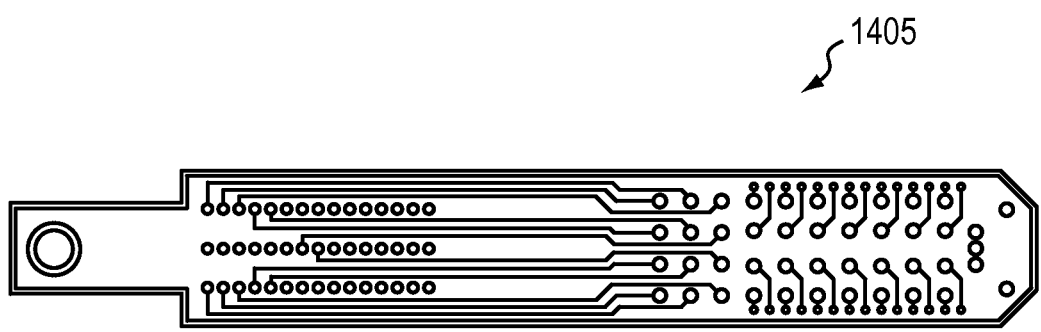

The performance of the sensor system was evaluated by fabricating and testing several devices. FIG. 14A illustrates a three-dimensional CAD model of one test device 1400, which includes a potassium-selective ISE half-cell formed in a single well of the device 1400. The ISE half-cell includes an ion-to-electron transducer layer (which includes a silver chloride layer) disposed over a silver-coated PCB electrode and capped with a hydrogel saturated with a salt solution of 3.0 molar KCl in water (functioning as the ion-selective membrane). FIG. 14B illustrates a wiring diagram 1405 for the test device 1400.

Figures 15A, 15B:
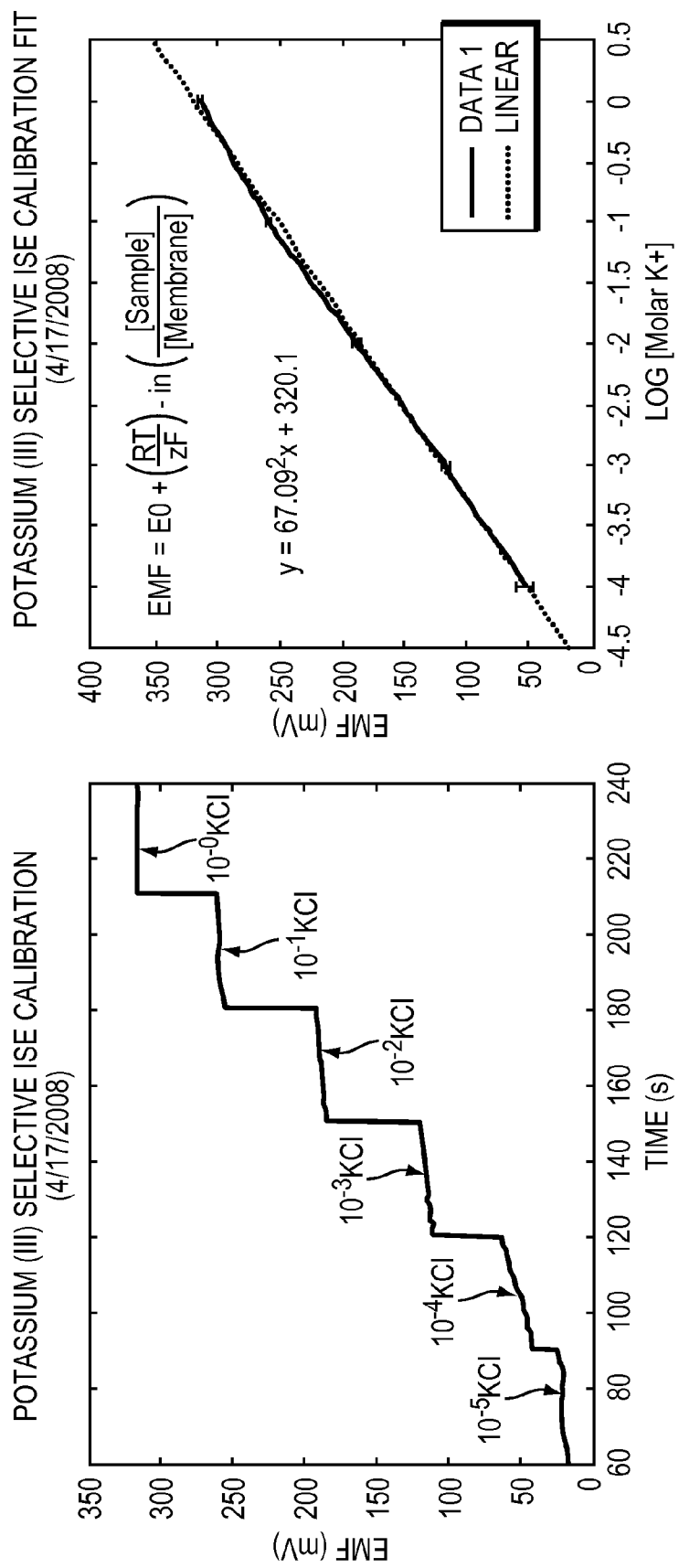
FIGS. 15A, 15B, 16A, and 16B are graphs illustrating exemplary results in accordance with embodiments of the invention.
Figure 16B:
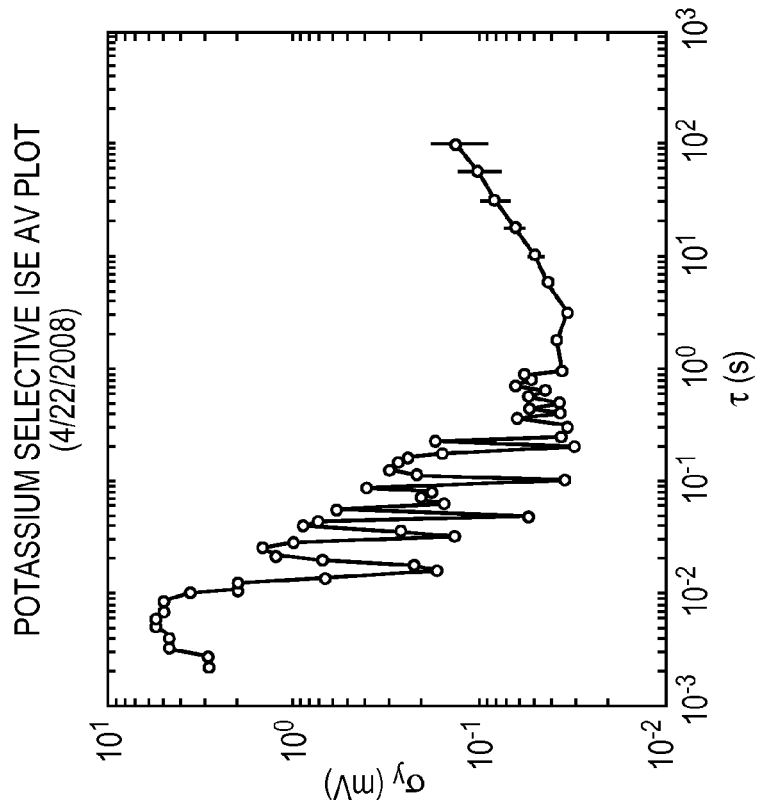
Figure 16A:
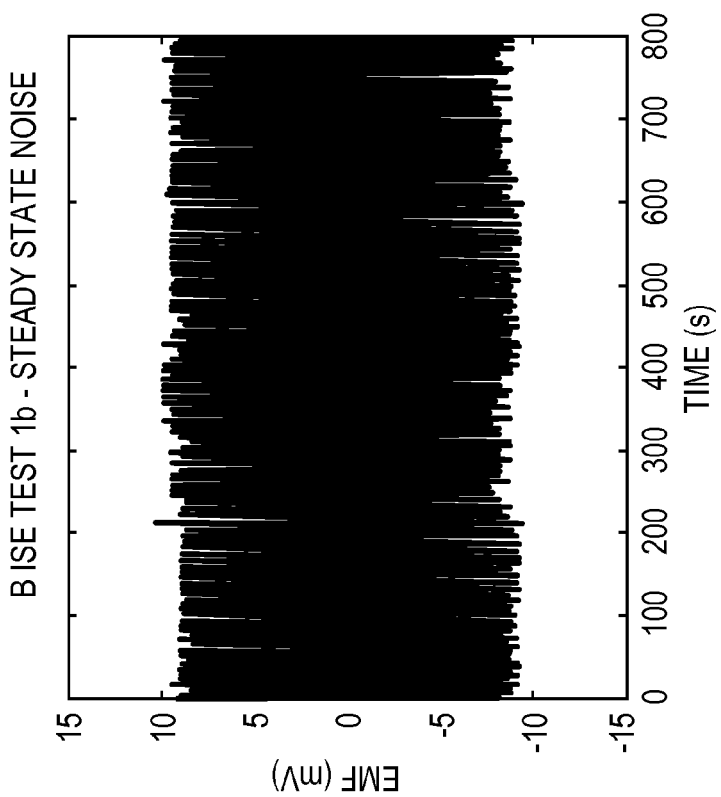

The electro-chemical performance of the ISE half-cell device 1400 was analyzed by generating a concentration-dependant response curve and measuring the steady-state EMF drift. FIGS. 15A and 15B illustrate that the sensor showed highly Nernstian log-linear behavior from $10^{-4}$ to $10^0$ molar potassium. The stability of the sensor was assessed by computing the Allan variance on EMF data recorded at 500 Hz for one hour. FIG. 16A illustrates the stead-state noise involved in the test, and FIG. 16B illustrates a variance plot showing an optimal sampling time of one second and a three-sigma drift of 3.78 mV/hr. This drift value is comparable to that of most large-scale, inner-filling-solution-based ISEs.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method of detecting an analyte, the method comprising:
   a) delivering an ambient comprising a first analyte and a second analyte to a plurality of sensors, wherein the ambient is a liquid or a gas and wherein each sensor comprises:
      a working electrode;
      an inner filling solution disposed in contact with the working electrode; and
      an ion-selective membrane disposed in contact with the inner filling solution, the ion-selective membrane (i) sealing the inner filling solution from the ambient and (ii) being in fluidic communication with a channel of a micro-fluidic front end that delivers the ambient;
   b) using the micro-fluidic front end to temporally separate the first and second analytes within the ambient such that the first analyte arrives at the plurality of sensors earlier than the second analyte; and
   c) measuring an electromotive force resulting from passage of the first analyte into the ion-selective membrane of at least one sensor.

2. The method of claim 1, wherein each of the plurality of sensors is disposed within a well over a substrate.

3. The method of claim 1, wherein the working electrode is an electrically conductive wire.

4. The method of claim 1, wherein the inner filling solution comprises a high-boiling point fluid.

5. The method of claim 1, wherein a cover is disposed over a sub-array of the plurality of sensors.

6. The method of claim 5, further comprising removing the cover before delivering the ambient comprising the first analyte to the plurality of sensors.

7. The method of claim 1, further comprising transmitting a signal corresponding to the electromotive force to a remote location.

8. The method of claim 1, further comprising measuring an electromotive force resulting from passage of the second analyte in the ambient through the ion-selective membrane of at least one sensor.

* * * * *